(12) United States Patent
Freyman

(10) Patent No.: US 7,218,962 B2
(45) Date of Patent: May 15, 2007

(54) MAGNETICALLY ENHANCED INJECTION CATHETER

(75) Inventor: Toby Freyman, Watertown, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 355 days.

(21) Appl. No.: 10/108,874

(22) Filed: Mar. 29, 2002

(65) Prior Publication Data
US 2003/0187320 A1 Oct. 2, 2003

(51) Int. Cl.
A61N 1/30 (2006.01)
A61N 1/00 (2006.01)
A61M 31/00 (2006.01)
A61M 37/00 (2006.01)

(52) U.S. Cl. ............. 604/21; 604/93.01; 604/264; 600/13

(58) Field of Classification Search .......... 604/890.1, 604/19–22, 48, 95.01, 95.04, 95.05, 131, 604/507–508, 157, 264, 528; 128/897–899; 600/9–15
See application file for complete search history.

(56) References Cited

U.S. PATENT DOCUMENTS

| | | | |
|---|---|---|---|
| 4,578,061 A | 3/1986 | Lemelson | |
| 5,273,525 A | 12/1993 | Hofmann | |
| 5,380,272 A | 1/1995 | Gross | |
| 5,401,239 A * | 3/1995 | Stephen et al. ............ 604/21 |
| 5,674,267 A | 10/1997 | Mir et al. | |
| 5,681,281 A | 10/1997 | Vigil et al. | |
| 5,702,359 A | 12/1997 | Hofmann et al. | |
| 5,713,863 A | 2/1998 | Vigil et al. | |
| 5,749,847 A | 5/1998 | Zewert et al. | |
| 5,851,218 A | 12/1998 | Lev | |
| 5,921,244 A * | 7/1999 | Chen et al. ............ 128/897 |
| 5,964,757 A | 10/1999 | Ponzi | |
| 5,999,847 A | 12/1999 | Elstrom | |
| 6,024,739 A | 2/2000 | Ponzi et al. | |
| 6,041,253 A | 3/2000 | Kost et al. | |
| 6,045,565 A | 4/2000 | Ellis et al. | |
| 6,048,337 A | 4/2000 | Svedman | |
| 6,056,743 A | 5/2000 | Ellis et al. | |
| 6,129,685 A * | 10/2000 | Howard, III ............ 600/585 |
| 6,142,939 A | 11/2000 | Eppstein et al. | |
| 6,149,641 A | 11/2000 | Ungs | |
| 6,181,964 B1 | 1/2001 | Hofmann et al. | |
| 6,210,392 B1 | 4/2001 | Vigil et al. | |
| 6,228,046 B1 | 5/2001 | Brisken | |
| 6,241,701 B1 | 6/2001 | Hofmann | |
| 6,248,112 B1 | 6/2001 | Gambale et al. | |
| 6,254,573 B1 | 7/2001 | Haim et al. | |
| RE37,463 E | 12/2001 | Altman | |
| 6,366,808 B1 | 4/2002 | Schroeppel et al. | |
| 6,544,163 B2 * | 4/2003 | Wallace et al. ............ 600/12 |
| 2002/0022799 A1 | 2/2002 | Apple | |
| 2003/0219785 A1* | 11/2003 | Hallahan et al. ............ 435/6 |

* cited by examiner

*Primary Examiner*—Catherine S. Williams
(74) *Attorney, Agent, or Firm*—Kenyon & Kenyon LLP

(57) ABSTRACT

A catheter adapted to deliver therapeutic or diagnostic agents to a target tissue of a human body is disclosed. A catheter in accordance with the present invention comprises a magnetic field source for directing the flow of the therapeutic of diagnostic agent. The therapeutic or diagnostic agent may be conjugated with diamagnetic particles, ferromagnetic particles, super paramagnetic particles, or paramagnetic particles.

23 Claims, 6 Drawing Sheets

MAGNETICALLY ENHANCED INJECTION CATHETER

FIELD OF THE INVENTION

The present invention relates generally to devices and methods for delivering therapeutic or diagnostic agents to a portion of the human body.

BACKGROUND OF THE INVENTION

Injection catheters are currently utilized in a wide variety of minimally invasive or percutaneous medical procedures. Generally, a catheter enables a physician to remotely perform a medical procedure by inserting the catheter into the vascular system of the patient at an easily accessible location and navigating the tip of the catheter to a desirable target site. By this method, virtually any target site in the patient's vascular system may be remotely accessed.

Typically, a percutaneous procedure begins with the step of inserting a distal portion of the catheter into the patient's vasculature at a convenient location. Once the distal portion of the catheter has entered the patient's vascular system the physician may urge the distal tip forward by applying longitudinal forces to the proximal portion of the catheter.

Injection catheters are a type of catheter which may be used to inject therapeutic or diagnostic agents into various target tissues within the human body. An advantage of injection catheters is that the target tissue may be accessed utilizing minimally invasive surgical techniques. As with other types of catheters, the physician typically is not able to manipulate the distal portion of an injection catheter directly.

In many applications the target tissue is within a wall of an organ such as the stomach or the heart. When the target tissue is within the wall of an organ it is often desirable to inject the therapeutic or diagnostic agent into the tissue proximate the center of the organ wall. If the needle of the injection catheter inadvertently passes through the wall, the therapeutic or diagnostic agents dispensed from the distal end of the needle will not be effectively delivered to the target tissue. Wall thickness may vary from organ to organ. Additionally, wall thickness may vary within one organ.

One example of a medical procedure involving the delivery of a therapeutic and/or diagnostic agent to a targeted portion of a patient's body is the treatment of esophageal varicies. This is a condition in which blood vessels of the esophagus are enlarged and may potentially burst. For such a procedure, a therapeutic agent is injected into the varix. When treating an esophageal varix, the agent may be a coagulant such as sodium morrhuate. When a coagulant is injected into a varix, it causes it to occlude. An injection catheter may be used to deliver the therapeutic agent in order to minimize the invasive nature of the procedure.

In a similar procedure, an injection catheter may be utilized in the treatment of ulcers in the stomach lining. With such treatment, an injection catheter may be used to deliver drugs such as sclerosing or vasoconstrictive agents. These drugs typically clot or occlude the bleeding tissue to stop bleeding or to reduce the possibility of a blood vessel bursting.

Injection catheters may also be used to inject therapeutic or diagnostic agents into the heart. Examples of agents delivered to the heart include genes, proteins, cells, genetically modified cells, or drugs. In the case of injecting a therapeutic agent into the heart, 27 or 28 gauge needles are generally used to inject solutions carrying genes, proteins, cells, or drugs directly into the myocardium. A typical volume of an agent delivered to an injection site is about 100 microliters. One factor limiting the efficiency of this delivery technique is the loss of therapeutic through ejection, after the needle is removed, during myocardial contraction.

Therapeutic and diagnostic agents may be delivered to a portion of the heart as part of a percutaneous myocardial revascularization (PMR) procedure. PMR is a procedure which is aimed at assuring that the heart is properly oxygenated. Assuring that the heart muscle is adequately supplied with oxygen is critical to sustaining the life of a patient. To receive an adequate supply of oxygen, the heart muscle must be well perfused with blood. In a healthy heart, blood perfusion is accomplished with a system of blood vessels and capillaries. However, it is common for the blood vessels to become occluded (blocked) or stenotic (narrowed). A stenosis may be formed by an atheroma which is typically a harder, calcified substance which forms on the walls of a blood vessel.

When techniques which treat individual lesions are not practical, percutaneous myocardial revascularization (PMR) may be used to improve the oxygenation of the myocardial tissue. A PMR procedure generally involves the creation of holes, craters or channels directly into the myocardium of the heart. In a typical PMR procedure, these holes are created using radio frequency energy delivered by a catheter having one or more electrodes near its distal end. After the wound has been created, therapeutic agents are sometimes injected into the heart chamber from the distal end of a catheter. A limitation of this procedure is that the therapeutic agent may be quickly carried away by the flow of blood through the heart or during contraction of the myocardium after the wound is formed.

SUMMARY OF THE INVENTION

The present invention relates generally to devices and methods for delivering therapeutic or diagnostic agents to a portion of the human body. In a particular application, the present invention relates generally to devices and methods for delivering and injecting therapeutic or diagnostic agents into heart tissue.

The present invention utilizes a magnetic field to improve the delivery of therapeutic or diagnostic agents. In an exemplary embodiment, the injection fluid comprises a therapeutic conjugated with magnetic particles, and the injection fluid is injected into a patient's tissue by an injection catheter that includes an elongated shaft having a lumen and a magnetic field source. The elongated shaft may include a point and an injection orifice proximate the distal end thereof. The magnetic field source may be an electromagnet or a permanent magnet.

In one embodiment, the fluid comprises a therapeutic conjugated with diamagnetic particles. In this embodiment, the magnetic field acts to repulse the fluid, thus the fluid is thrust further into the patient's tissue by the magnetic field created by the magnetic field source located on the catheter.

In another embodiment, the fluid comprises a therapeutic conjugated with ferromagnetic particles. In this embodiment, the magnetic field supplies a pulse which acts to aggregate the particles, decreasing loss of therautic through ejection by causing the particles to form a plug in the hole formed by the injection orifice in the tissue.

In another embodiment, the fluid comprises a therapeutic conjugated with paramagnetic or super paramagnetic particles. In this embodiment, the magnetic field source is an electromagnet located in the distal end of a second catheter that is positioned opposite the injection site in order to attract the therapeutic and pull it further into the tissue.

DETAILED DESCRIPTION

The following detailed description should be read with reference to the drawings, in which like elements in different drawings are numbered in like fashion. The drawings, which are not necessarily to scale, depict selected embodiments and are not intended to limit the scope of the invention. In some cases, the drawings may be highly diagrammatic in nature. Examples of constructions, materials, dimensions, and manufacturing processes are provided for various elements. Those skilled in the art will recognize that many of the examples provided have suitable alternatives which may be utilized.

Figure 1:
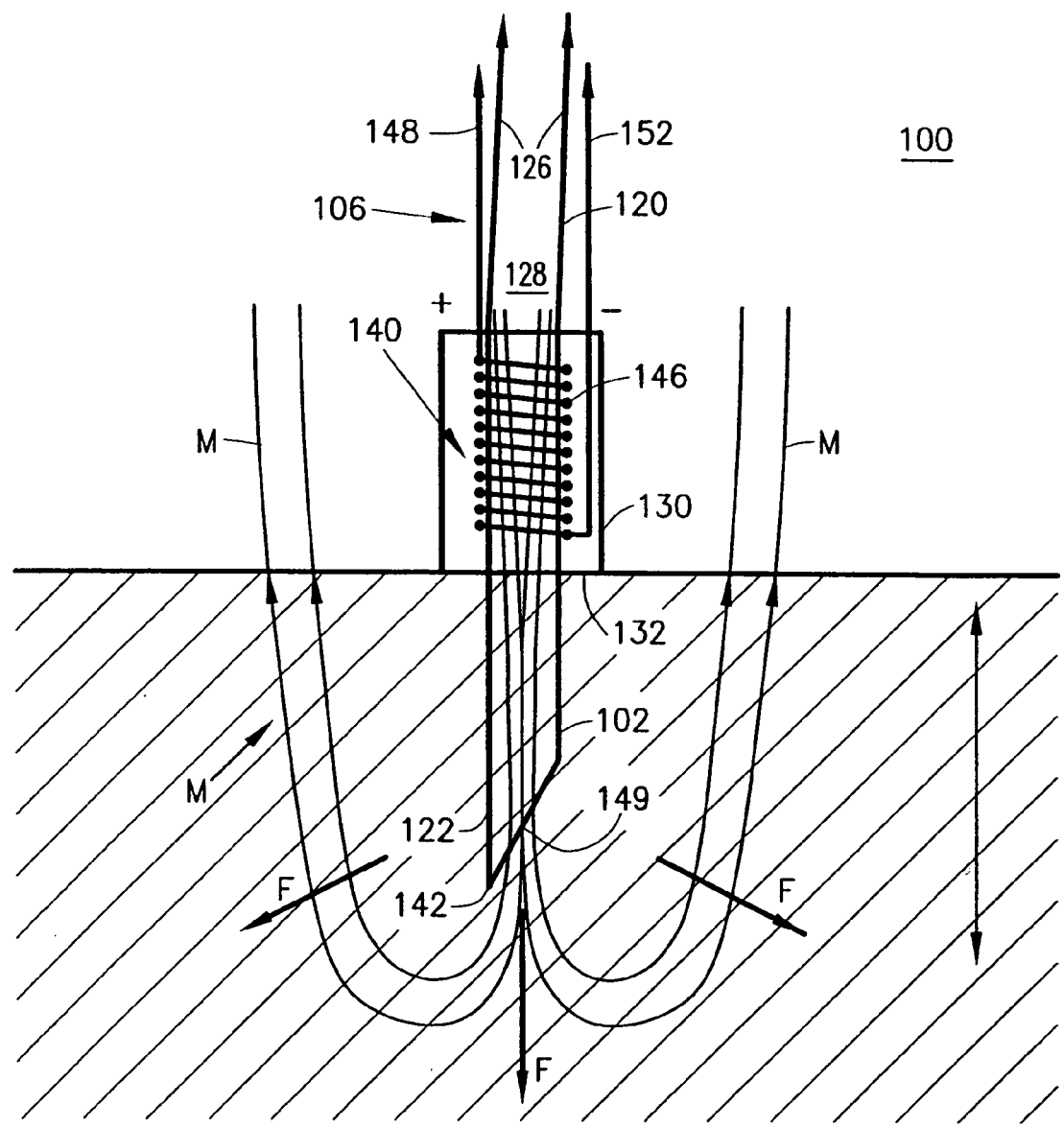
FIG. 1 is a plan view of a distal end of a catheter proximate to a patient's tissue in accordance with an exemplary embodiment of the present invention.

FIG. 1 is a plan view of a catheter 100 in accordance with the present invention. Catheter 100 has a distal end 102, a proximal end (not shown), and a shaft assembly 106. Shaft assembly 106 comprises a first elongated shaft 120 having a distal end 122, a proximal end (not shown), and an inside surface 126 defining a lumen 128. Shaft assembly 106 also includes a hood 130 disposed around the distal end 122 of first elongated shaft 120.

In the embodiment of FIG. 1, a magnetic field source 140 is disposed about the elongated shaft 120 and inside the hood 130. The magnetic field source 140 in this example is composed of a conductive coil 146 having a positive end 148 and a negative end 152 extending from the coil to the proximal end of the catheter.

In many applications it is desirable to advance distal end 122 of the elongated shaft 120 by a known distance relative to distal end 132 of the hood 130. In a preferred embodiment, a physician utilizing catheter 100 in a surgical procedure may advance distal end 122 of elongated shaft 120 from the proximal end of the catheter 100.

In the embodiment of FIG. 1, the elongated shaft 120 forms a point 142 near the distal end 122 thereof. The elongated shaft 120 also defines an injection port 144 proximate point 142. In a preferred embodiment, the injection port 144 is in fluid communication with the injection lumen 128.

Catheter 100 of FIG. 1 may be generally referred to as an injection catheter. In a preferred embodiment, elongated shaft 120 of catheter 100 comprises hypodermic tubing. The elongated shaft 120 may be constructed of any suitable material, including various metallic and nonmetallic materials, without deviating from the spirit and scope of the present invention. In cases where the elongated shaft 120 comprises a conductive material, insulating shielding may be necessary between the conductive material and the magnetic field source 140. Examples of metallic materials which may be suitable in some applications include stainless steel and nickel-titanium alloy.

The elongated shaft 120 may also be made from non-conductive material. Examples of nonmetallic materials which may be suitable in some applications are included in the list below, which is not exhaustive: polycarbonate, poly(L-lactide) (PLLA), poly(D,L-lactide) (PLA), polyglycolide (PGA), poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), polyD,L-lactide-co-caprol-actone) (PLA/PCL), poly(glycolide-co-caprolactone) (PGA/PCL), polyanhydrides (PAN), poly(ortho esters), poly(phosphate ester), poly(amino acid), poly(hydroxy butyrate), polyacrylate, polyacrylamid, poly(hydroxyethyl methacrylate), polyurethane, polysiloxane and their copolymers.

In the exemplary embodiment of FIG. 1, catheter 100 may be utilized to inject fluid into the myocardium tissue 111 of the heart of a patient. It is to be appreciated that catheter 100 may be utilized in the treatment of various medical conditions occurring in various locations in the body. For example, catheter 100 may be used in the treatment of esophageal varices, a condition in which blood vessels of the esophagus are enlarged and may potentially burst. For such a procedure, injection port 144 would be disposed proximate the enlarged varix and an appropriate agent would be injected into the varix. When treating an esophageal varix, the agent may be a coagulant such as sodium morrhuate. When a coagulant is injected into a varix, it causes the occlusion thereof.

In the exemplary embodiment shown in FIG. 1, the fluid comprises a therapeutic conjugated with diamagnetic particles. Thus, when a magnetic field is applied by the magnetic field source 140, the fluid is driven further into the target tissue as shown by the arrows F in FIG. 1. By modifying the strength and shape of the magnetic field, designated in FIG. 1 by the magnetic field lines M, produced by the magnetic field source 140, the direction and force with which the fluid is driven into the target tissue can be optimized for particular applications. For example, instead of using a magnetic field source comprising a cylindrical coil 146 as shown in FIG. 1, the coil 146 could be wound either more or less tightly or so that the central axis of the coil traces a loop or other desired shape.

Figure 2:
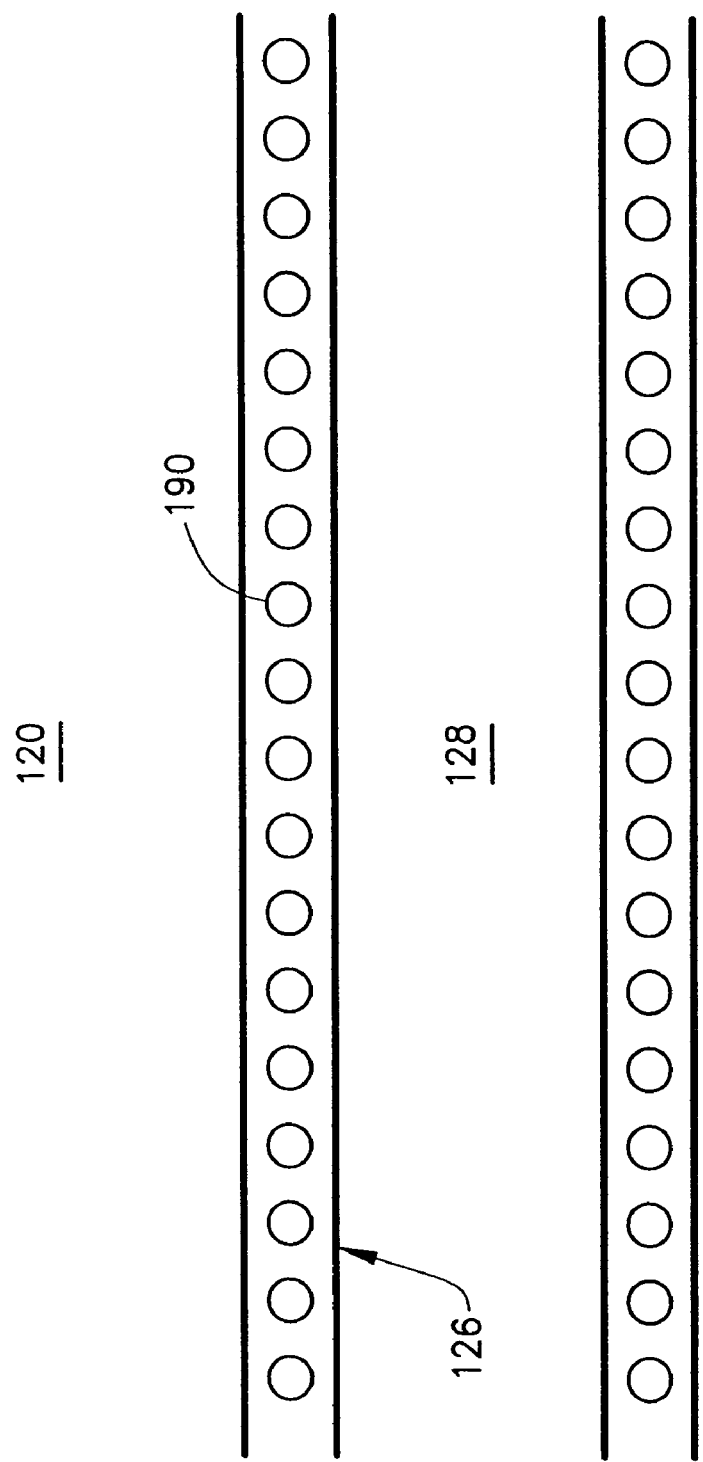
FIG. 2 is a cross-sectional view of a portion of an elongated shaft having a reinforcement member in accordance with an exemplary embodiment of the present invention.

In another embodiment, as shown in FIG. 2, the elongated shaft 120 of catheter 100 comprises an elongated tubular member including a reinforcement member 190 which may be, for example, braided or coiled wire. This reinforcement member 190 may be used as the magnetic field source by running a current through the wire of the reinforcement member 190 so that the reinforcement member 190 produces a magnetic field. Examples of metallic materials which may be suitable for the reinforcement member 190 in some applications include stainless steel and nickel-titanium alloy. Examples of non-metallic materials which may be suitable in some applications include: polyethylene (PE), polypropylene (PP), polyvinylchloride (PVC), polyurethane, polytetrafluoroethylene (PTFE), polyether block amide (PEBA), polyamide, and polyimide.

Figure 3:
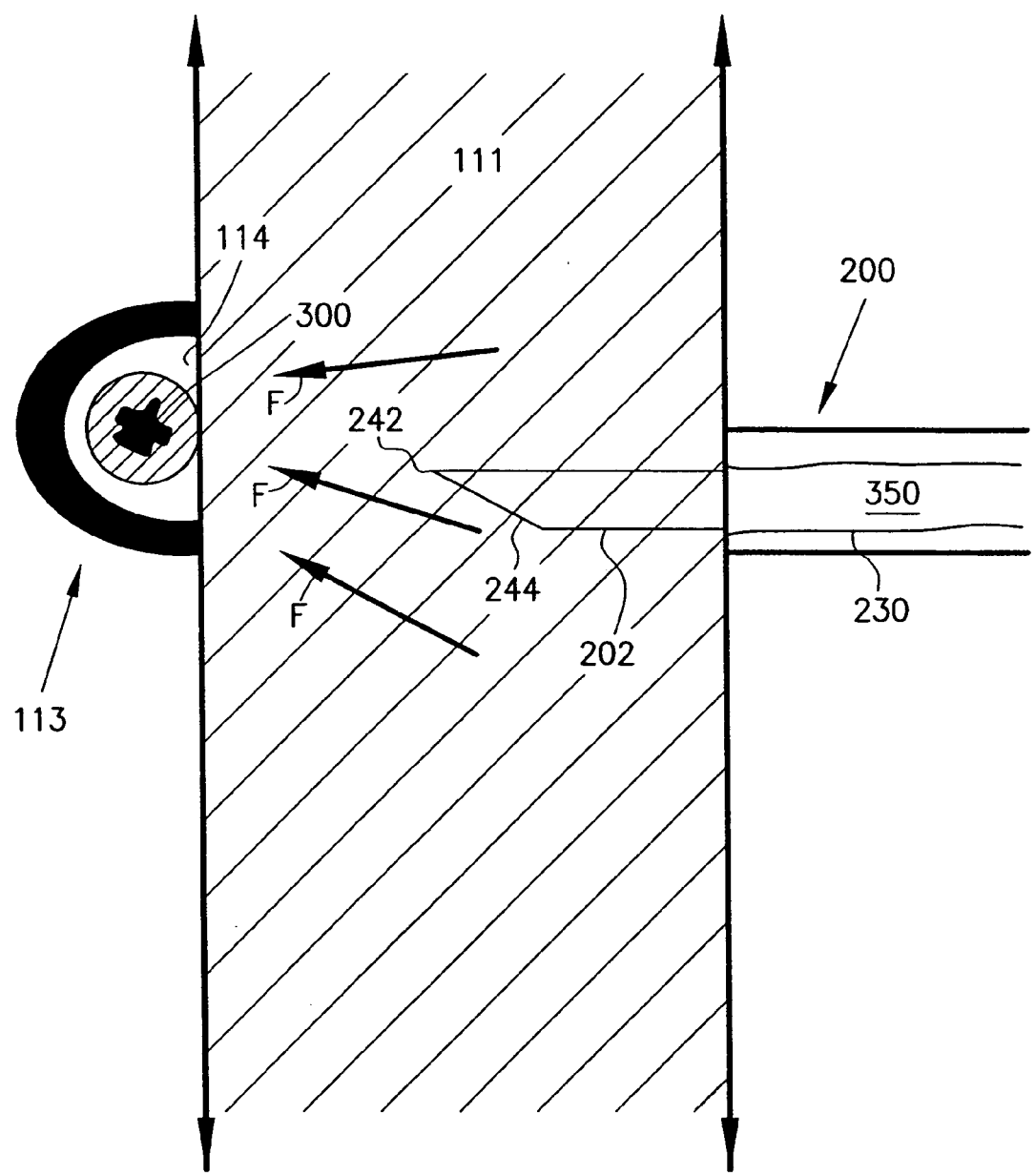
FIG. 3 is a diagrammatic view of a catheter in accordance with a second embodiment of the present invention within a patient.

FIG. 3 is a diagrammatic view showing catheters 200 and 300 inside the vascular system of a patient. The patient has tissue 111 and a vascular system including a blood vessel 113 defining a blood vessel lumen 114 where catheter 300 is located opposite the injection site. A second injection catheter 200 is used to inject therapeutic into the target tissue 111. As shown in FIG. 3, catheter 300 is disposed within blood vessel lumen 114 of blood vessel 113. Distal end 202 of catheter 200 is disposed within the target tissue 111.

A method of injecting a fluid into the target tissue 111 of patient may be described with reference to FIG. 3. The distal end of catheter 300 may be inserted into blood vessel lumen 114 of blood vessel 113. Distal end of catheter 300 may then be advanced through blood vessel lumen 114 of blood vessel 113. Catheter 300 may be urged forward through vascular system 112 until the distal end is proximate and opposite the injection site (e.g., a wall of heart 111).

The fluid injected into the target area may include various therapeutic or diagnostic agents adapted to treat any medical condition. It is to be appreciated that methods in accordance with the present invention may be used in the treatment of a number of medical conditions. For example, methods and devices for performing percutaneous myocardial revascularization (PMR) in accordance with the present invention have been envisioned. For example, a plurality of wounds may be created in hibernating tissue of the heart. These wounds may be created by injecting a fluid into the tissue of the heart. As a result of these wounds, there will be increased blood flow to the myocardium caused in part by the body's healing response to the wound. One healing response of the body is sometimes referred to as angiogenesis. In addition to promoting increased blood flow, it is also believed that PMR improves a patient's condition through denervation. Denervation is the elimination of nerves. The creation of wounds during this procedure results in the elimination of nerve endings which were previously sending pain signals to the brain as a result of hibernating tissue.

Suitable wounds may be created by injecting a fluid such as water, saline, or Ringer's solution into the heart tissue. Wound formation and revascularization of myocardial tissue may be enhanced by injecting a fluid including a therapeutic agent into the tissue of the heart. Examples of therapeutic agents which may be suitable include growth factors, drugs, cells, genetically modified cells, and caustic agents. The fluid injected into the heart tissue may also include a radiopaque material. Injecting a radiopaque material into the wound effectively marks the locations which have been treated. This will aid the physician in procedures which are being performed percutaneously using fluoroscopic equipment.

Figure 4:
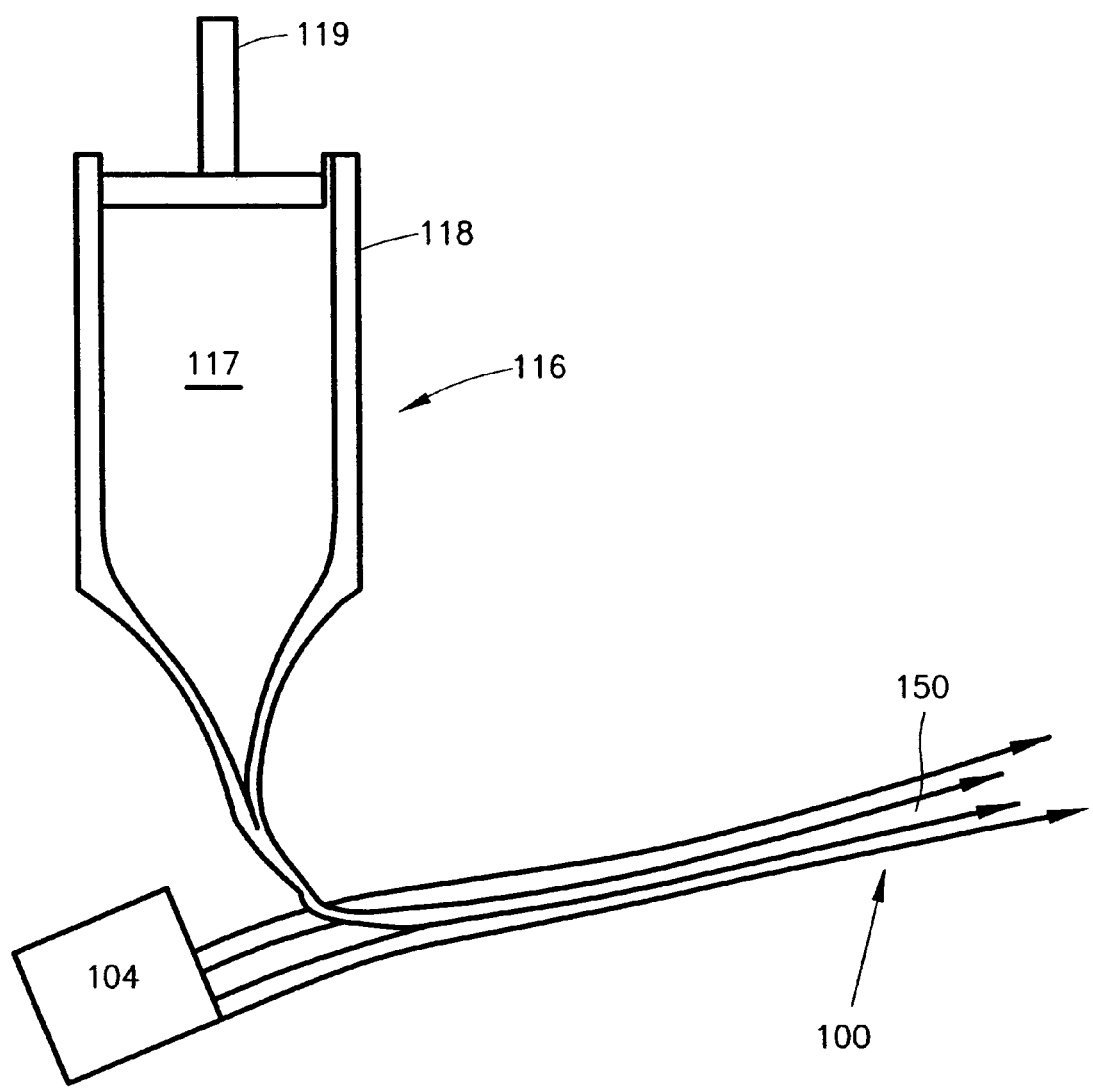
FIG. 4 is a diagrammatic view of the proximal end of a catheter in accordance with another embodiment of the present invention.

As shown in FIG. 4, a fluid source 116 may be coupled to the proximal end 104 of catheter 100. The fluid source 116 may include a variable volume chamber 117 defined by a body 118. In a preferred embodiment, variable volume chamber 117 is in fluid communication with an injection lumen 150. A plunger 119 is slidingly disposed within variable volume chamber 117. Urging the plunger distally has the effect of urging fluid into injection lumen 150. A number of energy sources may be utilized to urge plunger 119 distally. Energy sources which may be suitable in some applications include springs, compressed gas, a human being, magnetic force, gravity, and electricity.

Various additional embodiments of fluid source 116 are possible without deviating from the spirit and scope of the present invention. Examples of fluid sources which may be suitable in some applications include syringes, peristaltic pumps, and an IV bag with pressure applied to its outer surface.

Figure 5:
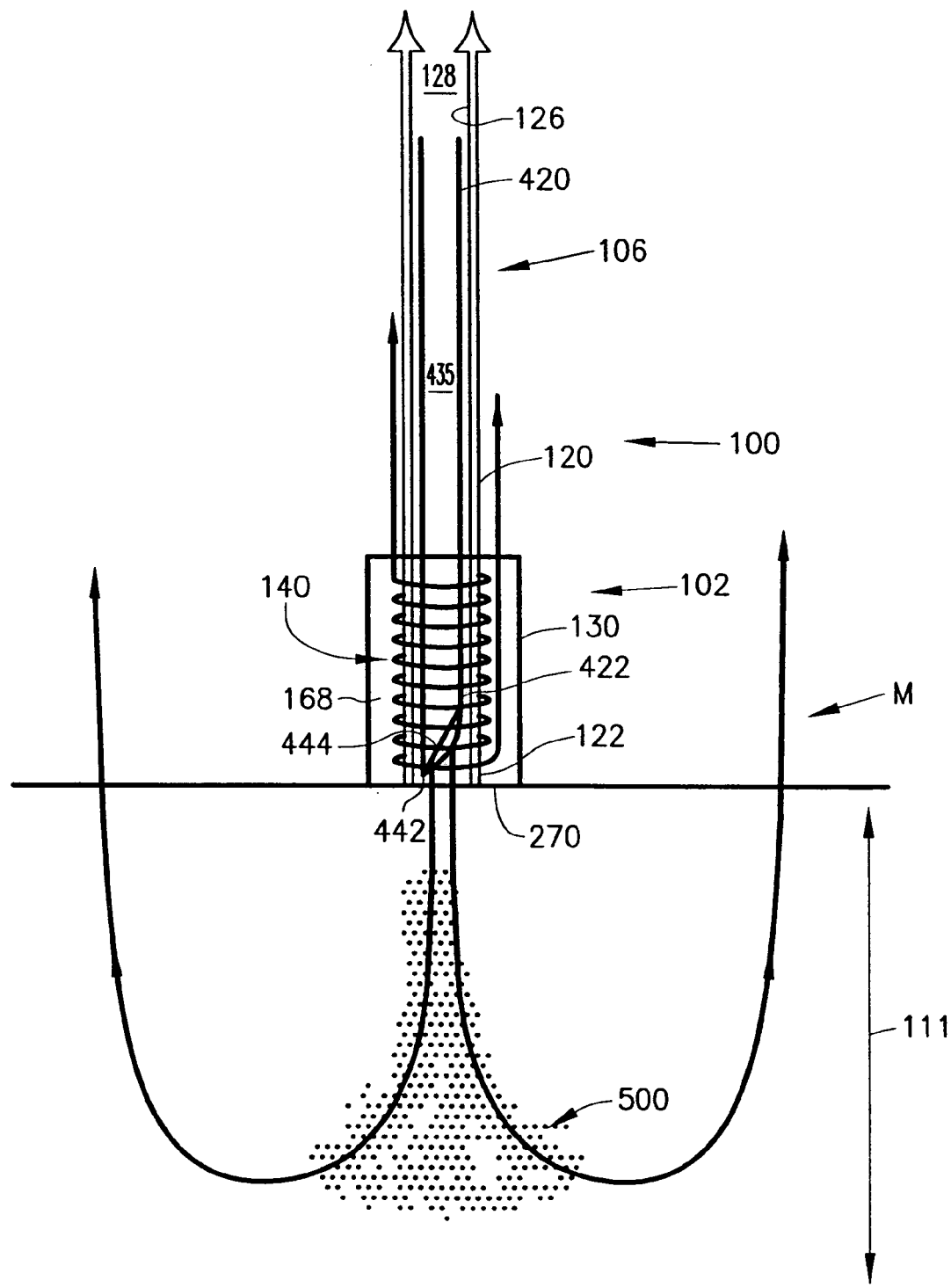
FIG. 5 is a cross-sectional view of a distal portion of a catheter in accordance with an embodiment of the present invention after injecting therapeutic into a patient's tissue.

FIG. 5 is a partial cross sectional view of a distal portion of an additional embodiment of a catheter 100 in accordance with the present invention. Catheter 100 includes a shaft assembly 106 comprising an elongated shaft 120 having a distal end 122 and an inside surface 126 defining a lumen 128. Shaft assembly 106 also includes a hood 130 disposed near and around the distal end 102 of the catheter 100.

The shaft assembly 106 may also include a second elongated shaft 420 disposed within the lumen 128 of the first elongated shaft 120 in order to allow an operator to vary the distance between a generally enlarged distal contact surface and the injection point. As shown in FIG. 5, second elongated shaft 420 is slidingly disposed within lumen 128. The distal end 422 of the second elongated shaft 420 is also disposed within the hood 130. In many applications it is desirable to advance distal end 422 of second elongated shaft 420 by a known distance relative to distal end 122 of first elongated shaft 120. In the embodiment of FIG. 5, second elongated shaft 420 may be selectively advanced and retracted.

The hood 130 also provides a generally enlarged distal contact surface 270. The generally enlarged distal contact surface 270 reduces the likelihood that undesired tissue damage will occur when the distal end 102 of catheter 100 is urged against bodily tissue. The hood 130 also defines a hood lumen 168.

In the embodiment of FIG. 5, second elongated shaft 420 forms a point 442 proximate distal end 422 thereof. Second elongated shaft 420 also defines an injection port 444 proximate point 442. Shaft 420 is advanced by a linear force applied to the proximal handle 104.

Once the injection port 444 penetrates the body tissue 111 at the target site, with injection port 444 of second elongated shaft 420 disposed within the target tissue, fluid may be urged into the target tissue by both the fluid pressure and the magnetic field source 140. For example, a force may be applied to a plunger urging fluid out of a fluid source and into injection lumen 428 of the second elongated shaft 420.

The fluid in this embodiment comprises a therapeutic conjugated with ferromagnetic particles 500. After this fluid is injected into the target tissue 111, the magnetic field source 140 located in the distal end of the catheter is turned on. The addition of fluid from fluid source together with the attractive, clumping force of the magnetic pulse on the ferromagnetic particles 500 conjugated with the therapeutic, results in the injection and retention of the fluid in the target tissue. Thus, when the injection port 444 is removed from the target tissue the fluid is prevented from leaking out of the hole formed by the injection port within the target tissue by the attractive magnetic force between the ferromagnetic particles.

Figure 6:
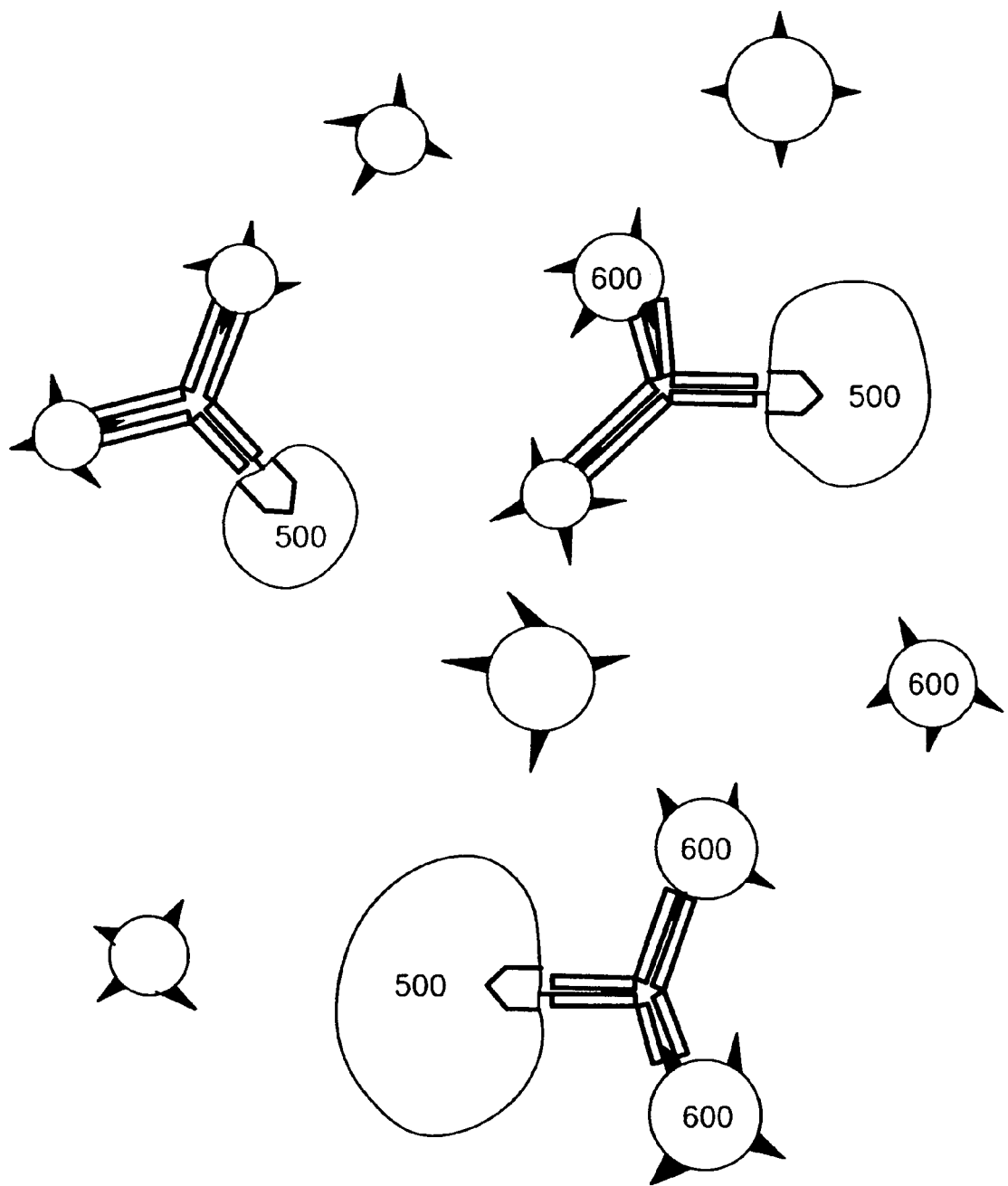
FIG. 6 is a schematic of magnetically conjugated particles in accordance with the present invention.

FIG. 6 is a schematic of a therapeutic 600 conjugated with magnetic particles 500. These particles comprise solid particles as small as a few tenths of a micrometer in diameter and having magnetic susceptibility. The solid particles may be diamagnetic (all materials are diamagnetic), ferromagnetic (such as iron and the rare earth elements), super paramagnetic (such as polymer materials containing iron oxide) or paramagnetic (such as oxygen, aluminum and any material having a net magnetic field). In addition to their geometric and magnetic properties, the solid particles are suitable for covalent or passive bonding to biologically active materials such as therapeutics. This conjugation of the magnetic particles to the therapeutic may be accomplished by hybridizing the magnetic particles with a polymer or coating the particle surface with antibodies or any other suitable method.

The therapeutic that may be deployed using the systems of the present invention can include numerous available therapeutics including pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral liposomes and cationic and anionic polymers and neutral polymers that are selected from a number of types depending on the desired application.

Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery mediated is formulated as needed to maintain cell function and viability.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor .alpha. and .beta. platelet-derived endothelial growth factor, platelet-derived growth factor, tumor necrosis factor .alpha., hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

Non-limiting examples of cells and genetically modified cells that may be appropriate for injection, include side population cells, lineage negative cells (Lin−), Lin−CD34, Lin−CD34+, Lin−cKit+, mesenchymal stem cells (MSC), cord blood cells, stem cells derived from cardiac or other tissue, whole bone marrow, bone marrow mononuclear cells, endothelial progenitor cells, skeletal myoblasts or satellite cells, muscle derived cells, Go cells, endothelial cells, adult cardiomyocytes, fibroblasts, smooth muscle cells, MSCs+5-aza, adult cardiac fibroblasts+5 aza, genetically modified cells, tissue engineered grafts, MyoD scar fibroblasts, pacing cells, embryonic stem cell clones, fetal or neonatal cells, immunologically masked cells, and teratoma derived cells. Side population cells may also be identified as Lin−, Sca-1+, c-Kit+, CD43+, CD45+, CD34−, according to surface protein identification.

Organs and tissues that may be treated by the methods of the present invention include any mammalian tissue or organ, injected in vivo. Non-limiting examples include heart, lung, brain, liver, skeletal muscle, smooth muscle, kidney, bladder, intestines, stomach, pancreas, ovary, prostate, eye, tumors, cartilage and bone.

Moreover, while no optical or sensory equipment has been described with any of these catheters, either optical and sensory equipment may be displaced through the catheters as required by the particular medical procedures being performed to assist the practitioner during the procedure.

Changes may be made in details, particularly in matters of shape, size, and arrangement of parts without exceeding the scope of the invention. The invention's scope is, of course, defined in the language in which the appended claims are expressed.

What is claimed is:

1. A catheter for injecting therapeutic into tissue, the catheter comprising:
   an elongated shaft having a proximal end, a distal end, a lumen extending therethrough; and
   a magnetic field source slidably coupled to the elongated shaft,
      wherein the magnetic field source is adapted to generate a magnetic field that affects movement of the therapeutic,
      wherein the magnetic field source comprises an electromagnet surrounding the elongated shaft.

2. The catheter of claim 1, further comprising:
   an electrical power lead connected to the magnetic field source;
      wherein the magnetic field source comprises a conducting coil of wire wound around the distal end of the catheter; and
   wherein the coil is in electrical contact with the electrical power lead.

3. The catheter of claim 1, wherein the distal end of the catheter comprises a material having a high magnetic induction.

4. The catheter of claim 1, further comprising a hood linked to the magnetic field source.

5. The catheter of claim 1, wherein the therapeutic is conjugated with magnetic particles.

6. The catheter of claim 1 wherein the lumen includes hypodermic tubing having a point.

7. The catheter of claim 6 wherein the magnetic field source is within a hood and wherein the point of the hypodermic tubing point is slidable from within the hood to beyond a distal end of the hood.

8. The catheter of claim 1 wherein the elongated shaft is a component of a percutaneous revascularization catheter.

9. The catheter of claim 1 further comprising insulating magnetic shielding between the magnetic field source and the elongated shaft.

10. A system for injecting therapeutic into tissue comprising:
    a catheter and a fluid to be injected by the catheter;
       wherein the catheter comprises:
          an elongated shaft having a proximal end, a distal end, and a lumen extending therethrough; and
          a magnetic field source coupled to the shaft, the magnetic field source moveable to different positions with respect to the lumen while coupled to the shaft, the magnetic filed source comprising an electromagnet, the magnetic field source surrounding the shaft,
             wherein the magnetic field source is adapted to generate a magnetic field to affect movement of the therapeutic; and
       wherein the fluid comprises:
          a therapeutic; and
          magnetic particles.

11. The system of claim 10, wherein the fluid comprises a therapeutic conjugated with diamagnetic particles.

12. The catheter of claim 10, wherein the fluid comprises a therapeutic conjugated with ferromagnetic particles.

13. The catheter of claim 10, wherein the fluid comprises a therapeutic and paramagnetic particles.

14. The system of claim 10 wherein the distal end of the catheter includes hypodermic tubing having a point.

15. The system of claim 14 wherein the magnetic field source is within a hood and wherein the point of the hypodermic tubing point is slidable from within the hood to beyond a distal end of the hood.

16. The system of claim 10 wherein the catheter is a percutaneous revascularization catheter.

17. The system of claim 10 further comprising magnetic insulating shielding between the magnetic field source and the elongated shaft.

18. An injection catheter for delivering therapeutic to a target tissue, comprising:
    a lumen having a piercing end;
    a magnetic field source surrounding the lumen, the magnetic field source moveable to different positions with respect to the lumen while coupled to the lumen; and
    a source of fluid in communication with the lumen,
       the fluid conjugated with magnetic particles.

19. The injection catheter according to claim 18 wherein the magnetic field source provides a magnetic field that orients magnetic particles released from the lumen and wherein the magnetic field source surrounds the lumen.

20. The injection catheter according to claim 18 wherein the magnetic field source is magnetically insulated from the injection catheter.

21. The injection catheter of claim 18 wherein the lumen includes hypodermic tubing having a point.

22. The injection catheter of claim 21 wherein the magnetic field source is within a hood and wherein the point of the hypodermic tubing point is slidable from within the hood to beyond a distal end of the hood.

23. The injection catheter of claim 18 wherein the lumen is within a percutaneous revascularization catheter.

* * * * *

UNITED STATES PATENT AND TRADEMARK OFFICE
CERTIFICATE OF CORRECTION

PATENT NO. : 7,218,962 B2  
APPLICATION NO. : 10/108874  
DATED : May 15, 2007  
INVENTOR(S) : Freyman It is certified that error appears in the above-identified patent and that said Letters Patent is hereby corrected as shown below:

Column 5, after line 20, the following paragraph should be inserted:

Once distal end of catheter 300 is positioned proximate and opposite the target tissue, the second injection catheter 200 may be advanced so that point 242 penetrates the bodily tissue at the target site. With injection port 244 of second catheter 200 disposed within the target tissue, fluid may be urged into the target tissue by both the fluid pressure and the magnetic field source 140 in catheter 300. For example, a force may be applied to a plunger in catheter 200, urging fluid out of a fluid source and into injection lumen 250 of elongated shaft 230. The magnetic field source on catheter 300 creates a magnetic field. In this embodiment, the injection fluid contains paramagnetic or super paramagnetic particles conjugates with therapeutic. The addition of fluid from fluid source together with the attractive force from the magnetic field source of catheter 300 acting on the paramagnetic particles, shown in Figure 3 with arrows F, results in the injection and retention of the fluid in the target tissue. As or after this fluid is injected into the target tissue, the magnetic field source located in the distal end of the catheter 200 is turned on. Thus, when the injection port 244 is removed from the target tissue, the fluid is prevented from leaking out of the hole formed by the injection port within the target tissue by the attractive magnetic force from the magnetic field source.

Column 1, line 46, "varicies" should be changed to --varices--;  
Column 4, lines 20-21, "polyD,L-lactide-co-caprol-actone)" should be changed to --poly(D,L-lactide-co-capro-lactone)--;  
Column 7, line 64, "endogeneus" should be changed to --endogenous--;

UNITED STATES PATENT AND TRADEMARK OFFICE
CERTIFICATE OF CORRECTION

PATENT NO. : 7,218,962 B2
APPLICATION NO. : 10/108874
DATED : May 15, 2007
INVENTOR(S) : Freyman It is certified that error appears in the above-identified patent and that said Letters Patent is hereby corrected as shown below:

Column 8, line 37, "("BMP's")" should be changed to --("BMPs")--;
Column 8, line 41, "BMP's" should be changed to --BMPs--; and
Claim 10, line 10 (column 10, line 4), "magnetic filed" should be changed to --magnetic field--.

Signed and Sealed this

Twenty-ninth Day of April, 2008

JON W. DUDAS
*Director of the United States Patent and Trademark Office*